US008241819B2

(12) United States Patent
Lowe et al.

(10) Patent No.: US 8,241,819 B2
(45) Date of Patent: Aug. 14, 2012

(54) METHOD FOR FORMING A VOLUME HOLOGRAPHIC SENSOR IN A POROUS MEDIUM

(75) Inventors: Christopher Robin Lowe, Cambridge (GB); Colin Alexander Bennett Davidson, Cambridge (GB); Jeffrey Blyth, Cambridge (GB); Satyamoorthy Kabilan, Cambridge (GB); Alexander James Marshall, Cambridge (GB); Blanca Madrigal Gonzalez, Cambridge (GB); Anthony Peter James, Cambridge (GB)

(73) Assignee: Smart Holograms Limited, Cambridge (GB)

( * ) Notice: Subject to any disclaimer, the term of this patent is extended or adjusted under 35 U.S.C. 154(b) by 0 days.

(21) Appl. No.: 12/340,104

(22) Filed: Dec. 19, 2008

(65) Prior Publication Data

US 2009/0098467 A1    Apr. 16, 2009

Related U.S. Application Data

(62) Division of application No. 10/509,781, filed as application No. PCT/GB03/01488 on Apr. 4, 2003, now abandoned.

(30) Foreign Application Priority Data

Apr. 5, 2002  (GB) .................................. 0207943.2

(51) Int. Cl.
*G03H 1/02*     (2006.01)
(52) U.S. Cl. ..................................... 430/1; 430/2; 359/3
(58) Field of Classification Search .................. None
See application file for complete search history.

(56) References Cited

U.S. PATENT DOCUMENTS

| | | | | |
|---|---|---|---|---|
| 3,027,336 A | * | 3/1962 | Gotz et al. | ..................... 521/117 |
| 4,588,664 A | * | 5/1986 | Fielding et al. | ..................... 430/1 |
| 4,742,086 A | | 5/1988 | Masamizu et al. | |
| 4,753,717 A | | 6/1988 | Yata et al. | |
| 4,842,968 A | | 6/1989 | Kojima et al. | |
| 4,970,129 A | * | 11/1990 | Ingwall et al. | ..................... 430/1 |
| 5,198,912 A | * | 3/1993 | Ingwall et al. | ..................... 359/3 |
| 5,352,582 A | | 10/1994 | Lichtenwalter et al. | |
| 5,989,923 A | | 11/1999 | Lowe et al. | |
| 6,239,224 B1 | | 5/2001 | Mørk et al. | |
| 6,303,290 B1 | * | 10/2001 | Liu et al. | ........................... 435/4 |
| 6,461,873 B1 | | 10/2002 | Catania et al. | |

(Continued)

FOREIGN PATENT DOCUMENTS

JP    61-218640    *    3/1985

(Continued)

OTHER PUBLICATIONS

Mayes et al. "A holographic alcohol sensor" Anal. Chem., vol. 71(16) pp. 3390-3396 (Aug. 1999).*

(Continued)

*Primary Examiner* — Martin Angebranndt
(74) *Attorney, Agent, or Firm* — Saliwanchik, Lloyd & Eisenschenk

(57) ABSTRACT

A sensor for the detection of an analyte, comprising a holographic element comprising a medium and a hologram disposed throughout the volume of the medium, wherein an optical characteristic of the hologram changes as a result of a variation of a physical property occurring throughout the volume of the medium, wherein the medium is obtainable by formation in situ in the presence of a pore-forming agent, wherein the agent is not present in the sensor or does not react with the analyte and the sensor.

8 Claims, 1 Drawing Sheet

U.S. PATENT DOCUMENTS

Figure 1:
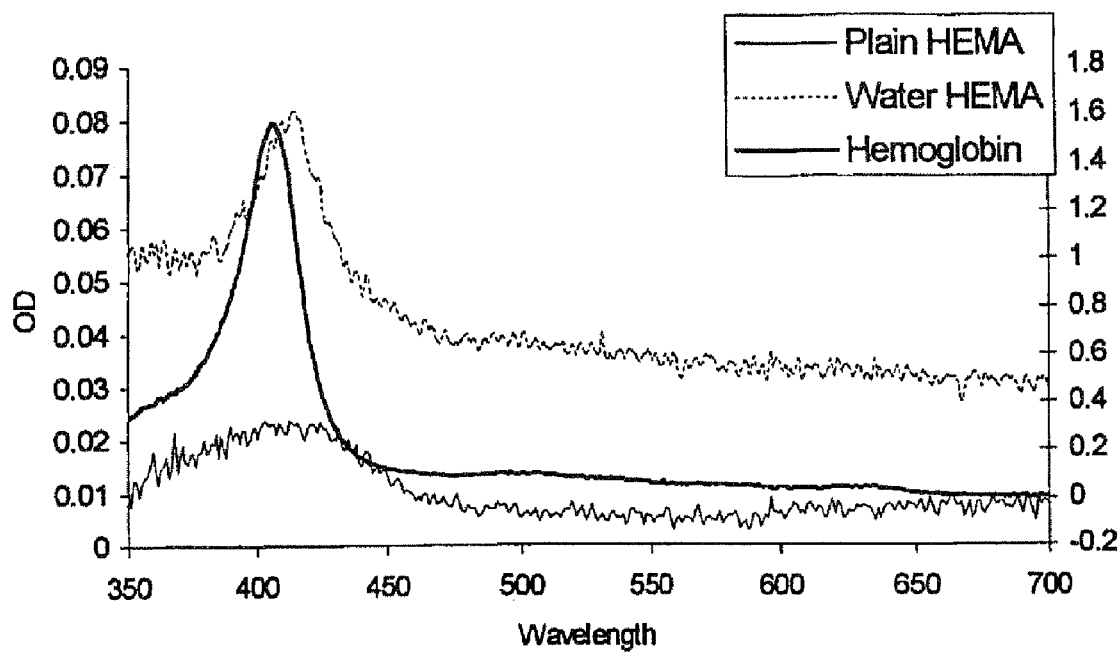

| | | | |
|---|---|---|---|
| 6,528,167 B2 | 3/2003 | O'Gara | |
| 6,689,316 B1 | 2/2004 | Blyth et al. | |
| 7,186,567 B1 * | 3/2007 | Sutherland et al. | 436/532 |

FOREIGN PATENT DOCUMENTS

| | | | |
|---|---|---|---|
| JP | 62-106902 | * | 5/1987 |
| JP | 2584261 | | 6/1989 |
| JP | 01 148267 | | 9/1989 |
| JP | 2001-098102 | * | 4/2001 |
| SU | 1255450 | | 9/1986 |
| WO | WO 99/63408 | | 12/1999 |
| WO | WO 01/44813 | | 6/2001 |

OTHER PUBLICATIONS

Chirilla et al. "Hydrophillic sponges based on 2-hydroxyethyl methacrylate . . . " Polym. Int., vol. 32 pp. 221-232 (1993).*

Dusek et al. "Phase separation in poly(2-hydroylethyl methacrylate .." Eur. Polym. J., vol. 7 pp. 1275-1285 (1971).*

Yacoubin et al., "Holographic recording on 2-hydroxymethacrlyate . . . " Proc. SPIE vol. 1559 pp. 403-409 (1991).*

Smirnova "Photopolymer for holography: interconnection between holographic . . . " Proc. SPIE vol. 3733 pp. 364-373 (Jun. 1999).*

Kuma kura et al."Polymeric matwerials having a porous structures . . . " J. Mater. Sci., vol. 19(5) pp. 1616-1621 (1984).*

Mayes et al. "A holographic sensor based on a rationally designed synthetic polymer" J. Mol. Recog., vol. 11 pp. 168-174 (1998).*

Sutherland et al. "Electrically switchable volume gratings in polymer dispersed liquid crystals", Appl. Phys. Lett., vol. 64(9) pp. 1074-1076 (Feb. 1994).*

Bunning et al. "The morphology and performance of holographic transmission gratings . . . " Polymer vol. 36(14) pp. 2699-2708 (1995).*

Wang et al. "preparation of porous polyurethane particles and their use in enzyme immobilization" Biotechnol. Prog., vol. 9 (6) pp. 661-665 (1993).*

Mikos et al., "Formation of highly porous biodegradable scaffolds for tissue engineering", Electron. J. Biotech. vol. 3(2) pp. 115-119 (2000).*

Chen et al., "Generation of porous polymer surfaces by solvent-nonsolvent treatment" J. App. Poly. Sci., vol. 45 pp. 377-386 (1992).*

Kim et al., "Conformational properties of isotactic poly(2-hydroxyehyl methacrylate) in mixed water-alcohol solvents", J. Poly. Sci., Pt. A., Poly. Chem., vol. 25 pp. 467-474 (1987).*

Database, Section Ch, Week 198717, Derwent Publications Ltd., London, GB; AN 1987-121289, Abstract in English for SU 1 255 450 A (Kazan Eng. Cons. Inst.), Sep. 7, 1986.

Patent Abstracts of Japan, Vo. 013, No. 408 (C-634), Sep. 8, 1989, English abstract of JP 01 148267.

Ley, C. et al., "Holographic gratings recorded in polymer hydrogels—an original application as a sensor in aqueous environment," *Meas. Sci. Technol.*, 1997, vol. 8, pp. 997-1000.

* cited by examiner

METHOD FOR FORMING A VOLUME HOLOGRAPHIC SENSOR IN A POROUS MEDIUM

This application is a divisional application of application Ser. No. 10/509,781, filed Jan. 3, 2006, now abandoned; which is a National Stage Application of International Application Number PCT/GB03/01488, filed Apr. 4, 2003; which claims priority to United Kingdom Application No. 0207943.2, filed Apr. 5, 2002, each of which is incorporated herein by reference in its entirety.

FIELD OF THE INVENTION

This invention relates to a sensor based on a sensitive element which is a hologram.

BACKGROUND TO THE INVENTION

WO-A-9526499 discloses a holographic sensor, based on a volume hologram. This sensor comprises an analyte-sensitive matrix having an optical transducing structure disposed throughout its volume. Because of this physical arrangement of the transducer, the optical signal generated by the sensor is very sensitive to volume changes or structural rearrangements taking place in the analyte-sensitive matrix as a result of interaction or reaction with the analyte.

An alternative method of production for a holographic sensor is disclosed in WO-A-9963408. A sequential treatment technique is used, wherein the polymer film is made first and sensitive silver halide particles are added subsequently. These particles are introduced by diffusing soluble salts into the polymer matrix where they react to form an insoluble light-sensitive precipitate. The holographic image is then recorded.

SUMMARY OF THE INVENTION

An aspect of the invention is a sensor for the detection of an analyte, which comprises a holographic element. The element comprises a hologram disposed throughout the volume of a support medium, wherein an optical characteristic of the hologram changes as a result of a variation of a physical property occurring throughout the volume of the medium. The medium is obtainable by formation in situ, preferably by the polymerisation of monomers in the presence of a pore-forming agent. Though present and active in the polymerisation process, the agent is not present in the sensor and/or does not react with the analyte or the sensor. The agent may be a gas, liquid or solid; a solid may be extracted to produce pores.

The formation of additional and/or larger pores in the matrix allows greater diffusion of the analyte throughout the support medium, thus making the sensor more responsive to changes in analyte concentration.

DESCRIPTION OF THE PREFERRED EMBODIMENTS

A holographic sensor generally comprises a holographic support medium and, disposed throughout the volume of the medium, a hologram. The support medium interacts with an analyte resulting in a variation of a physical property of the medium. This variation induces a change in an optical characteristic of the holographic element, such as its polarisability, reflectance, refractance or absorbance. If any change occurs whilst the hologram is being replayed by incident broad band, non-ionising electromagnetic radiation, then a colour or intensity change, for example, may be observed.

There are a number of basic ways to change a physical property, and thus vary an optical characteristic. The physical property that varies is preferably the size of the holographic element. This may be achieved by incorporating specific groups into the support matrix, wherein these groups undergo a conformational change upon interaction with the analyte, and cause an expansion or contraction of the support medium. A group is preferably the specific binding conjugate of an analyte species. Another method would be to change the active water content of the support medium.

A holographic sensor may be used for detection of a variety of analytes, simply by modifying the composition of the support medium. The medium preferably comprises a polymer matrix the composition of which must be optimised to obtain a high quality film, i.e. a film having a uniform matrix in which holographic fringes can be formed. The matrix is preferably formed from the copolymerisation of (meth)acrylamide and/or (meth)acrylate-derived monomers, and may be cross-linked. In particular, the monomer HEMA (hydroxyethyl methacrylate) is readily polymerisable and cross-linkable. PolyHEMA is a versatile support material since it is swellable, hydrophilic and widely biocompatible.

Other examples of holographic support media are gelatin, K-carageenan, agar, agarose, polyvinyl alcohol (PVA), sol-gels (as broadly classified), hydro-gels (as broadly classified), and acrylates. Further materials are polysaccharides, proteins and proteinaceous materials, oligonucleotides, RNA, DNA, cellulose, cellulose acetate, siloxanes, polyamides, polyimides and polyacrylamides. Gelatin is a standard matrix material for supporting photosensitive species, such as silver halide grains. Gelatin can also be photo-cross-linked by chromium III ions, between carboxyl groups on gel strands.

When the analyte is relatively large in relation to the dimensions of the pores in the polymer matrix and/or the polymer has little or no associated porosity, diffusion of the analyte into and throughout the matrix is inhibited. Thus the sensor may become slower to respond to changes in analyte concentration.

A sensor of the invention comprises a holographic support medium, which may be formed by the polymerisation of monomers or comonomers in the presence of an agent which produces a porous polymer matrix. The agent may be optimally selected for producing pores of a specific dimension. This is particularly relevant when the analyte is sterically bulky, e.g. large biological molecules such as haemoglobin.

The pore-forming agent or porogen may be a liquid, gas or solid, e.g. of particles such as bicarbonate, carbonate or PVC. When solid particles are used, they are preferably insoluble in the polymerisation mixture, such that post-polymerisation they are still present in the matrix, from which they can subsequently be removed by reaction (e.g. acid), dissolution or rinsing. When the agent is a gas, this may be bubbled through the polymerisation mixture.

An example of a pore-producing agent is water. By incorporating water into a monomer mixture, such as HEMA monomers, small pockets may be produced during the polymerisation process, resulting in a more porous polymer matrix.

For example, the agent may be a non-solvent for the polymer. Another example is a salt which can be present in high concentration during polymerisation. A metal alginate could be used, and removed by washing with EDTA/acid (to take out the metal) followed by dissolution. A protein or liquid may be removed enzymatically. The agent may also be removed by physical methods, e.g. laser irradiation or ablation. A UV absorber could be heated locally, using local differences in temperature to cause pore formation.

The agent may be a gas, which could be generated in situ. Electrolysis or physical movement may stimulate gas formation in a suitable system. If the matrix incorporates a solvent saturated with gas, removal of the solvent will generate bubbles. Bubble formation may be stabilised by the presence of a surfactant such as Pluronic.

The following Examples illustrate the invention.

EXAMPLE 1

A polymer matrix was formed by polymerisation of HEMA monomers in water and 4% methanol (w/v). For reference, a polymer was made by polymerisation of HEMA monomers in isopropanol. Upon formation, each polymer was soaked for 2 hours in 50 mg/ml haemoglobin, and the respective absorption spectra were determined, as shown in FIG. 1. The absorption spectrum of a control solution of 0.25 mg/ml of haemoglobin is also shown for comparison.

The presence of water in the polymerisation mixture resulted in a more porous polymer matrix. As shown in the absorption spectra, the increased porosity of the matrix allows greater diffusion of the relatively large haemoglobin molecules, producing an absorption correlating more closely to that of the haemoglobin solution.

EXAMPLE 2

A pair of holographic polymer matrices were produced, each having a monomer composition of 70% HEMA, 20% ethylene dimethacrylate (EDMA) and 10% methacrylic acid (MAA). One of the polymers was produced by polymerisation of the monomers in propanol; the other in water and 8% methanol (w/v). Holographic recording material was then disposed on each support, and the holograms recorded.

Figure 2:
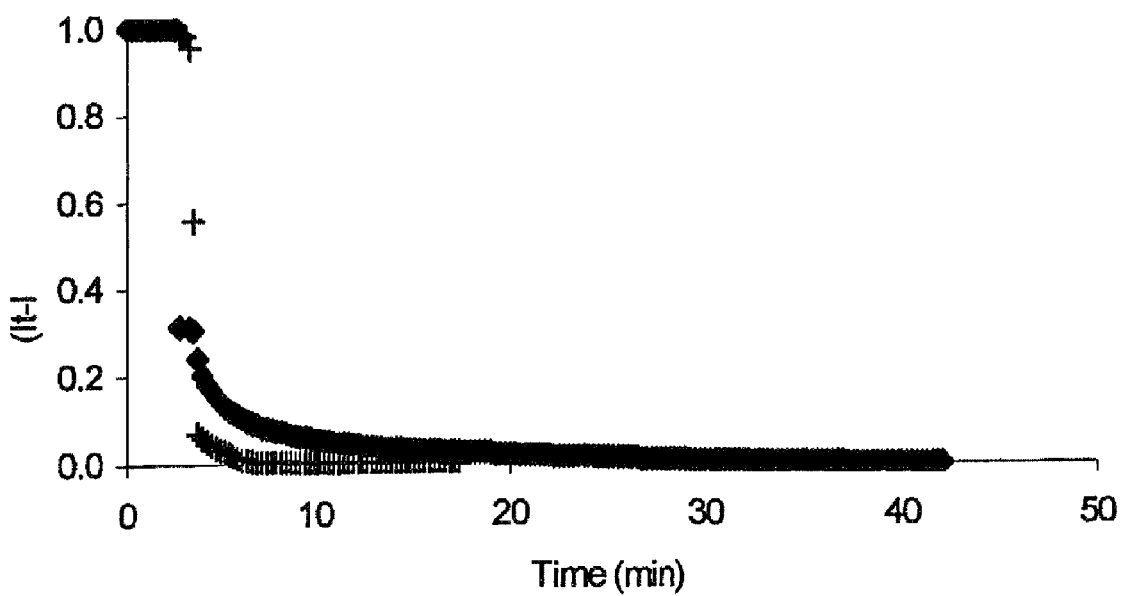

The developed holograms were immersed in an analyte sample. The response times to increasing analyte concentration are shown in FIG. 2. The presence of water in the polymerisation mixture produced a microporous polymer structure, resulting in a more responsive holographic sensor.

We claim:

1. A method for preparing a sensor, wherein the sensor comprises a holographic element comprising a medium and a reflection hologram disposed throughout the volume of the medium, wherein an optical characteristic of the reflection hologram changes as a result of a variation of a physical property occurring throughout the volume of the medium, the method comprising:
    forming the medium by polymerization of monomers or comonomers in the presence of water and methanol, whereby removal of the water forms pores in the polymer;
    removing the water so that it is not present in the sensor, to produce a porous medium, and
    forming a reflection hologram in the porous medium;
    wherein pores of the porous medium are sized to accommodate a large biological molecule, and
    wherein the pores of the porous medium allow diffusion of the large biological molecule into and throughout the porous medium.

2. The method, according to claim 1, wherein the physical property is the size of the medium.

3. The method, according to claim 1, wherein the optical characteristic is the reflectance, refractance or absorbance of the holographic element.

4. The method according to claim 1, wherein the monomers include hydroxyethyl methacrylate.

5. The method, according to claim 1, wherein the medium is a cross-linked polymeric medium.

6. The method, according to claim 1, wherein the pores are sized to accommodate hemoglobin.

7. The method according to claim 1, wherein the monomers or comonomers are polymerized in a mixture of the water and the methanol in which the water is 96% (w/v) of the mixture.

8. The method according to claim 1, wherein the monomers or comonomers are polymerized in a mixture of the water and the methanol in which the water is 92% (w/v) of the mixture.

* * * * *